(12) United States Patent
Kronberg et al.

(10) Patent No.: US 6,537,536 B1
(45) Date of Patent: Mar. 25, 2003

(54) COMMODE ODOR PREVENTOR

(76) Inventors: Paul T. Kronberg, 15 Fieldbrook Rd., Clinton, CT (US) 06413; Brett M. Kronberg, 19 Tuttle Pl., East Haven, CT (US) 06512

( * ) Notice: Subject to any disclaimer, the term of this patent is extended or adjusted under 35 U.S.C. 154(b) by 12 days.

(21) Appl. No.: 09/618,078

(22) Filed: Jul. 17, 2000

(51) Int. Cl.⁷ .................. A61L 9/00; A61L 9/01
(52) U.S. Cl. .................. 424/76.1; 424/76.21; 424/76.4; 424/76.5; 424/76.6; 424/400; 424/405; 424/406
(58) Field of Search .................. 424/76.1, 76.21, 424/76.4, 76.5, 76.6, 400, 405, 406

(56) References Cited

U.S. PATENT DOCUMENTS 5,984,993 A * 11/1999 Mainz et al. .................. 71/12
6,051,215 A * 4/2000 van Njinatten et al. .... 424/76.1

* cited by examiner

*Primary Examiner*—Thurman K. Page
*Assistant Examiner*—Liliana Di Nola-Baron
(74) *Attorney, Agent, or Firm*—Robert H. Montgomery

(57) ABSTRACT

An agent for preventing generation of noxious odors in a commode which provides an energy source for bacteria to the exclusion of sulfates for a period of time and comprises a mixture of one of calcium nitrate, $CaN_2O_6$, or calcium nitrate tetra hydrate, $CaN_2O_6.4H_2O$, and ammonium nitrate, $NH_4NO_3$. A mixture is prepared using 200–1000 grams of calcium nitrate or 1.37(200–1000) grams of tetra hydrate and 1.25 to 12 grams of ammonium nitrate in de-ionized water having a ph of 5 to 9 to produce one liter of the mixture. A fragrance and a coloring agent may optionally be added. The resulting mixture is then mixed one-half ounce to one liter or one-half gallon of water. This will keep the commode fresh without change for a period of twenty-four to thirty-six hours.

13 Claims, No Drawings

COMMODE ODOR PREVENTOR

FIELD OF THE INVENTION

This invention relates to odor preventors for commodes of the type, which are used by physically impaired and/or incontinent persons who are not able to immediately move a distance required to reach a toilet.

BACKGROUND OF THE INVENTION

The term commode as used herein refers to a non-plumbed toilet including an open top pot or bucket or similar container which receives excrement which must be periodically removed, emptied and cleansed. The content of the container is disposed of in a toilet or other excrement disposal receptacle connected to a sewer or septic system.

Commodes are used in private homes, convalescent homes, hospitals, etc. for the elderly, incontinent and/or physically impaired. In many cases, it is not convenient or possible to empty the content of the commode each time it is used.

Noxious odors, primarily hydrogen sulfate gas, emanate from a commode due to excrement therein. This odor develops from bacteria feeding on sulfates in liquid in the commode and the generation of hydrogen sulfate gas. This leads to the necessity of emptying and cleaning the commode container after short intervals of time. It is common practice to attempt to combat these odors by using an antibacterial agent to kill the bacteria. Formaldehyde base agents kill the bacteria, but this stops the excrement from decomposing and is detrimental to a septic system. Oil based chemicals do not mix with water and are not environmentally acceptable.

Accordingly, the present invention provides a new odor preventing agent for commodes, and method of using same which provides an energy source for bacteria, which the bacteria feed on for an extended period of time and does not lead to the production of noxious gases during such extended period of time.

In the commode liquid, bacteria run out of gaseous oxygen which is an energy source. The bacteria are capable of obtaining oxygen from sulfates and as they consume sulfates they generate hydrogen sulfide gas resulting in the noxious gas.

It has been determined that some organisms (anerobes and facultative anerobes) are capable of obtaining oxygen, as an energy source, from nitrates or sulfates in the absence of gaseous oxygen. Commode bacteria will use nitrates as an energy source in preference to sulfates.

An agent embodying the invention, which contains nitrates, does not produce any scent when fed upon by the bacteria; thus, no noxious odor of a sulfate gas is formed.

An object of this invention is to provide a new and improved agent that will prevent odor emanating from a commode for a long period of time after initial use.

Another object of this invention is to provide a new and improved odor preventing agent for a commode and method of using same, which supplies an energy source other than sulfates for bacteria to feed on.

Another object of the invention is to provide a new and improved odor preventing agent which will permit a commode, or in emergencies a toilet, to have its excrement contents to remain non-disposed of for an extended period of time without the emission of noxious odors during the extended period of time.

A further object of this invention is to provide an odor-preventing agent for commodes, which is environmentally safe and will not adversely affect bacteria in a septic system upon disposal of the contents of the commode container.

SUMMARY OF THE INVENTION

Briefly stated, the invention in one form thereof, comprises a mixture of a nitrate, for example one of calcium nitrate, $CaN_2O_6$, or calcium nitrate tetra hydrate, $CaN_2O_6 \cdot 4H_2O$, (hereinafter "tetra hydrate") and ammonium nitrate, $NH_4NO_3$. A mixture is prepared using 200–1000 grams of calcium nitrate or 1.37(200–1000) grams of tetra hydrate and 1.25 to 12 grams of ammonium nitrate in water having a pH of 5 to 9 to produce one liter of the mixture. A preferred mixture is hereinafter described. A fragrance and a coloring agent may optionally be added. The resulting mixture is then mixed one-half ounce to one liter or one-half gallon of water when applied to a commode. As the bacteria feed on the nitrates, decomposition of the nitrates does not generate any noxious odors. This will keep the commode fresh without change for twenty-four to thirty-six hours until the bacteria have depleted the nitrates.

The invention is particularly pointed out and distinctly claimed in the concluding portion of this specification. The invention, however, together with further objects and advantages thereof may be best appreciated by reference to the following detailed description.

DETAILED DESCRIPTION OF PREFERRED EMBODIMENTS OF THE INVENTION

A mixture embodying the invention predominantly comprises one or more compounds, which bacteria will feed upon to the exclusion of sulfates without generating a noxious odor. Briefly stated, the invention in one form thereof is a mixture comprised of 200 to 1000 grams of calcium nitrate, $CaN_2O_6$, and 1.25 to 12 grams of ammonium nitrate, $NH_4NO_3$ or $H_4N_2O_3$. Alternatively, calcium nitrate tetra hydrate, $CaN_2O_6 \cdot 4H_2O$, may be used instead of calcium nitrate. This substitution may be made in the interest of economy and when made the tetra hydrate is substituted in the ratio of substantially 1.37:1 for calcium nitrate. The calcium nitrate is in a powdered state and the tetra hydrate is in a crystal state. These ingredients are mixed with water having a pH of 5 to 9, preferably as close to a pH of 7 as possible, to yield one liter of solution.

The calcium nitrate or tetra hydrate provides an energy source for bacteria that will feed on this compound to the exclusion of sulfates until the nitrates are depleted. As the nitrates approach the lower end of the stated range, the nitrates will be depleted sooner and the bacteria will then commence to feed on sulfates. As the calcium nitrate is increased toward the upper end of the range the agent becomes more expensive.

The ammonium nitrate is provided in relatively limited quantity to control the growth of bacteria. If the growth of bacteria is not controlled they will multiply system when the content of the commode bucket is emptied and reaches a septic system. The ammonium nitrate is a bacteria or bacteria count control agent.

A balance must be reached that will provide no generation of noxious odors for a selected period of time, but which will not be harmful to the bacteria of a septic system. The period of time may be extended by increasing the amount of calcium nitrate. However, this may be detrimental if the bacteria are allowed to multiply. If the amount of the ammonium nitrate is correspondingly increased to control the growth of bacteria, the pH of the solution will be increased killing off a large quantity of bacteria and leaving a residue, which is detrimental to the bacteria in a septic system.

A preferred mixture is as follows:

432 grams of calcium nitrate or equivalent tetra hydrate (×1.37)

5 grams of ammonium nitrate

Mix these quantities with water having a ph of 5 to 9 to obtain a one liter liquid solution. If a fragrance is desired add one ounce of Carrubba fragrance No. B9421WS. If a masking color is desired for aesthetics, add twenty-four (24) to thirty (30) drops of color dye, as for example, Chromatech No. L85010 Royal Blue Lot No. Z1052.

This resulting mixture is then bottled. When a commode container is emptied and cleaned, before further use, add one-half ounce of the resulting mixture to one-half gallon or one liter of water.

Tests have shown that this mixture will last twenty-four to thirty six hours and the rate of bacteria growth is suitable to an acceptable negative factor. For example using the mixture set forth above resulted in a drop in bacteria plate count from $4 \times 10^6$ to $2.4 \times 10^6$ per milliliter.

This will keep the commode odor free for twenty-four (24) to thirty-six (36) hours, dependent on use, until the bacteria nitrate energy source is depleted.

The invention is primarily directed to use in commodes as described above, however, in an emergency when toilets are not flushable the invention will have application. Such emergency may occur where a home of other facility is dependent on well water and there is an electric outage rendering a well pump inoperative.

An essential feature of the invention is providing a bacteria energy source for the bacteria to the exclusion of sulfates. It has been found that the most economical bacteria nutrients are nitrates particularly calcium nitrates.

The calcium nitrate or tetra hydrate may be mixed with the ammonium nitrate within the stated ratios and marketed in dry form with instructions for mixing with the proper amount of water prior to use. Additionally, the calcium nitrate and tetra hydrate may be combined in the quantities to obtain the desired results. In the specific example, 216 grams of calcium nitrate may be combined with 1.37(216) grams of tetra hydrate and the result mixed with the ammonium nitrate.

It may thus be seen that the objects of the invention set forth above as well as those made apparent are efficiently attained. While preferred embodiments of the invention have been set forth for purposes of disclosure, modifications to the disclosed embodiments as well as other embodiments of the invention may occur to those skilled in the art. Accordingly, the appended claims are intended to cover all modifications to the disclosed embodiments of the invention as well as other embodiments thereof which do not depart from the spirit and scope of the invention.

What is claimed is:

1. A mixture for preventing noxious odors in commodes which comprises one or more compounds which are a bacteria energy source which bacteria will feed to the exclusion of sulfates and a bacteria count control agent in a liquid solution, said mixture comprising in proportion about 200–1000 grams of calcium nitrate or about 1.37(215–1200) grams of calcium nitrate tetra hydrate as the energy source and about 1.25–12.0 grams of ammonium nitrate in about one liter of water.

2. The mixture of claim 1 further comprising a fragrance.

3. The mixture of claim 1 further comprising a coloring agent.

4. The mixture of claim 1 comprising about 432 grams of calcium nitrate or 1.37(432) grams of calcium tetra hydrate and about 5 grams of ammonium nitrate in one liter of water.

5. A method of preventing noxious odors in a commode comprising the steps of providing in liquid form a mixture containing an energy source for bacteria to the exclusion of sulfates and an agent for controlling the growth of bacteria in a limited quantity to prevent increase in bacteria plate count in the commode but which is not deleterious to a septic system, combining said mixture with water and combining a quantity of said mixture in liquid form with water in the commode.

6. The method of claim 5 wherein the nutrient is calcium nitrate or calcium nitrate tetra hydrate and the agent for controlling the growth of bacteria is ammonium nitrate.

7. The method of claim 6 further including a step of introducing a fragrance into the mixture.

8. The method of claim 6 further including the step of introducing a coloring agent in the mixture.

9. A method of preventing noxious odors in a commode comprising the steps of mixing about 200–1000 grams of calcium nitrate or about 1.37(200–1000) grams of calcium nitrate tetra hydrate with about 1.25–12.0 grams of ammonium nitrate in about one liter of water with a pH of 5–9 and dispensing about one liquid ounce of the resulting mixture in a commode with about two liters of water.

10. The method of claim 7 wherein the step of mixing comprises using about 432 grams of calcium nitrate or about 1.37(432) grams of calcium nitrate tetra hydrate and about 5 grams of ammonium nitrate.

11. The method of claim 9 further including the step of including a fragrance in the mixture.

12. The method of claim 9 further including the step of including a coloring agent in the mixture.

13. The method of claim 9 further including the step of including a fragrance in the mixture.

* * * * *